US008887317B2

(12) United States Patent
Hirsch (10) Patent No.: US 8,887,317 B2
(45) Date of Patent: Nov. 18, 2014

(54) PROTECTIVE GARMENT WITH SCISSOR DEFLECTING AND JAMMING OBSTACLES (71) Applicant: Yuval Hirsch, Herzeliya (IL)

(72) Inventor: Yuval Hirsch, Herzeliya (IL)

( * ) Notice: Subject to any disclaimer, the term of this patent is extended or adjusted under 35 U.S.C. 154(b) by 78 days.

(21) Appl. No.: 13/847,141

(22) Filed: Mar. 19, 2013

(65) Prior Publication Data
US 2014/0283272 A1 Sep. 25, 2014

(51) Int. Cl.
A41B 9/12 (2006.01)
F41H 1/02 (2006.01)
A41D 13/05 (2006.01)

(52) U.S. Cl.
CPC .......................................... F41H 1/02 (2013.01)
USPC .............. 2/406; 2/408; 2/464; 2/2.5; 128/883

(58) Field of Classification Search
None
See application file for complete search history.

(56) References Cited

U.S. PATENT DOCUMENTS

| | | | | |
|---|---|---|---|---|
| 2,396,599 A * | 3/1946 | O'Brien | .......................... | 2/408 |
| 2,443,474 A * | 6/1948 | Morgan | .............................. | 2/67 |
| 2,790,973 A * | 5/1957 | Lewis, Jr. et al. | .................. | 2/2.5 |
| 2,879,654 A * | 3/1959 | Evans | .............................. | 66/176 |
| 3,279,469 A * | 10/1966 | Schustack | ....................... | 450/113 |
| 3,490,224 A * | 1/1970 | Bourgeas | ....................... | 57/210 |
| 3,501,774 A * | 3/1970 | Norman | .............................. | 2/321 |
| 3,771,171 A * | 11/1973 | Mitchell | ............................. | 2/2.5 |
| 3,787,892 A * | 1/1974 | Quinn | .............................. | 2/466 |
| 3,788,314 A * | 1/1974 | Noreen | .............................. | 602/67 |
| 3,829,899 A * | 8/1974 | Davis | ................................. | 2/2.5 |
| 3,883,898 A * | 5/1975 | Byrnes, Sr. | ....................... | 2/167 |
| 3,953,893 A * | 5/1976 | Byrnes, Sr. | .......................... | 2/51 |
| 4,004,295 A * | 1/1977 | Byrnes, Sr. | .......................... | 2/16 |
| 4,014,044 A * | 3/1977 | Figueroa et al. | ................... | 2/466 |
| 4,035,844 A * | 7/1977 | Atack et al. | ....................... | 2/466 |
| 4,164,217 A * | 8/1979 | Schrock | ........................ | 128/883 |
| 4,244,367 A * | 1/1981 | Rollenhagen | ................. | 604/396 |
| 4,316,286 A * | 2/1982 | Klein | ................................. | 2/2.5 |
| 4,384,449 A * | 5/1983 | Byrnes et al. | .................... | 57/210 |
| 4,441,211 A * | 4/1984 | Donzis | ............................... | 2/459 |
| 4,599,751 A * | 7/1986 | Bouwhuis | .......................... | 2/400 |
| 4,688,269 A * | 8/1987 | Maeshima | ......................... | 2/456 |
| 4,732,803 A * | 3/1988 | Smith, Jr. | ....................... | 428/212 |
| 4,737,401 A * | 4/1988 | Harpell et al. | ................ | 442/187 |

(Continued)

FOREIGN PATENT DOCUMENTS

| | | | |
|---|---|---|---|
| CA | 2343707 A1 | 5/2000 | |
| CA | 2343707 C | 5/2000 | |

(Continued)

Primary Examiner — Bobby Muromoto, Jr.
(74) Attorney, Agent, or Firm — Lyman Moulton, Esq.; Moulton Patent, PLLC (57) ABSTRACT A protective garment and undergarment with scissor deflecting and jamming obstacles includes strapping having the obstacles in series patterned to be parallel to a strap thereof and have parallel and angular surfaces thereto configured to deflect a pair of commercial scissor blades into an angle of incidence to the strap. A spacing between obstacles is also configured to be less than a total thickness of the scissor blades in order to jam the scissors there between and impede or deter an assault of the wearer. The garment also includes a waist strap, a crotch strap and thigh straps disposed at an outer respective edge to of the garment. Each strap includes a non-elastic material and the cut-resistant obstacle strapping permanently disposed there around configured to deflect a pair of scissors into an obstacle cutting position or jam the pair of scissors on an obstacle thereof and impede or deter an assault.

17 Claims, 8 Drawing Sheets

(56) References Cited

U.S. PATENT DOCUMENTS

| | | | |
|---|---|---|---|
| 4,738,893 A * | 4/1988 | Grillo | 442/246 |
| 4,802,242 A * | 2/1989 | Lars-Jos | 2/2.5 |
| 4,810,559 A * | 3/1989 | Fortier et al. | 428/161 |
| 4,835,795 A * | 6/1989 | Lonon | 2/408 |
| 4,884,295 A * | 12/1989 | Cox | 2/467 |
| 4,912,781 A * | 4/1990 | Robins et al. | 2/2.5 |
| 4,916,000 A * | 4/1990 | Li et al. | 428/105 |
| 4,922,899 A * | 5/1990 | Graff et al. | 602/72 |
| 4,981,147 A * | 1/1991 | Barnett | 128/842 |
| 5,014,354 A * | 5/1991 | Dumont | 2/23 |
| 5,210,877 A * | 5/1993 | Newman | 2/456 |
| 5,485,636 A * | 1/1996 | Yandell | 2/406 |
| 5,539,927 A * | 7/1996 | Holubec | 2/69 |
| 5,572,737 A * | 11/1996 | Valice | 2/465 |
| 5,613,251 A * | 3/1997 | Yandell | 2/338 |
| 5,636,387 A * | 6/1997 | Lundy | 2/408 |
| 5,754,982 A * | 5/1998 | Gainer | 2/2.5 |
| 5,806,295 A * | 9/1998 | Robins et al. | 57/220 |
| 6,324,699 B1 * | 12/2001 | Cosmah | 2/239 |
| 6,453,791 B1 * | 9/2002 | Seitzinger | 2/2.5 |
| 6,668,868 B2 * | 12/2003 | Howland et al. | 139/383 R |
| 6,782,559 B2 * | 8/2004 | Regan | 2/455 |
| 6,792,620 B2 * | 9/2004 | Green | 2/69 |
| 6,961,958 B1 * | 11/2005 | Seitzinger | 2/2.5 |
| 7,010,811 B1 * | 3/2006 | Park | 2/2.5 |
| 7,100,352 B2 * | 9/2006 | Robins | 57/210 |
| 7,168,101 B2 * | 1/2007 | Guma | 2/408 |
| 7,810,167 B2 * | 10/2010 | Seitzinger et al. | 2/2.5 |
| 8,418,262 B2 * | 4/2013 | Angus | 2/2.5 |
| 8,561,213 B2 * | 10/2013 | Howell et al. | 2/2.5 |
| 8,671,462 B2 * | 3/2014 | Garcia et al. | 2/2.5 |
| 8,763,167 B2 * | 7/2014 | Howell et al. | 2/466 |
| 2001/0029621 A1 * | 10/2001 | Howland et al. | 2/2.5 |
| 2002/0035755 A1 * | 3/2002 | Widdemer | 8/94.15 |
| 2002/0073473 A1 * | 6/2002 | Bachner et al. | 2/2.5 |
| 2003/0056275 A1 * | 3/2003 | Regan | 2/78.1 |
| 2005/0009424 A1 * | 1/2005 | Hazan et al. | 442/50 |
| 2005/0155336 A1 * | 7/2005 | Robins | 57/210 |
| 2007/0271965 A1 * | 11/2007 | Kolmes et al. | 66/170 |
| 2008/0206526 A1 * | 8/2008 | Kim et al. | 428/195.1 |
| 2008/0289087 A1 * | 11/2008 | Sundnes | 2/456 |
| 2009/0301139 A1 * | 12/2009 | Kolmes et al. | 66/185 |
| 2009/0311930 A1 * | 12/2009 | Wang et al. | 442/134 |
| 2010/0050699 A1 * | 3/2010 | Kolmes et al. | 66/174 |
| 2010/0058812 A1 * | 3/2010 | Schulein et al. | 66/171 |
| 2010/0175430 A1 * | 7/2010 | Garcia et al. | 66/174 |
| 2010/0227143 A1 * | 9/2010 | Mulholland | 428/220 |
| 2010/0263109 A1 * | 10/2010 | Noerenberg et al. | 2/456 |
| 2011/0131706 A1 * | 6/2011 | Andersson | 2/239 |
| 2011/0167545 A1 * | 7/2011 | Garcia et al. | 2/455 |
| 2012/0023641 A1 * | 2/2012 | Shen et al. | 2/122 |
| 2014/0182038 A1 * | 7/2014 | Hirsch | 2/2.5 |

FOREIGN PATENT DOCUMENTS

| | | |
|---|---|---|
| CN | 2247429 Y | 2/1997 |
| DE | 4324398 A1 | 1/1995 |
| DE | 19948051 | 4/2001 |
| KR | 20090069670 | 7/2009 |

* cited by examiner

PROTECTIVE GARMENT WITH SCISSOR DEFLECTING AND JAMMING OBSTACLES

BACKGROUND OF THE INVENTION

Much can be said about the necessity to protect teenage girls and women from being sexual assaulted and raped. Indeed there are various products on the market that address this issue. However, it seems that none of the offered products are truly effective because rapes and assaults are not prevented, much less deterred by products commercially available. In fact, there does not appear to be any correlation between assaults and rape and any preventive products available in the market today.

There are essentially two ways of providing protection for women: active and passive protection. Active products are based on action from the victim and include pepper spray, tear gas, and electro shock, weapons, etc. These products have limited affect since they depend on the courage and resourcefulness of the victim but also may allow the attacker to use the product against the victim.

Other products which offer passive protection are not dependent on the skill of the victim. However, such passive protection may cause serious injuries to the attacker such as the anti-rape female condom and an anti-rape tampon. Because some passive protection devices may be intrusive to the victim's comfort and privacy, such devices are not therefore very popular in the market either.

Another type of passive protection is the protective underwear or shorts. Otherwise known as chastity belts, protective underwear are typically cumbersome and made of bulky and non-ergonomic materials. Protective underwear is often therefore not used when a woman goes jogging, plays sports and goes walking but those are times when a woman may need protection most.

However, such products can't be practically worn under clothing and are therefore not for daily use. What is needed in the market is a form-fitting and comfortable protective garment that may be worn every day and be easily laundered. There has therefore been a long felt need for an ergonomic and versatile protective garment that gives women a high degree of confidence and security for everyday use against assault and rape.

SUMMARY OF THE INVENTION

A protective garment of elastic ergonomic material covering a wearer from his or her waist to their thighs comprises straps having obstacles patterned to be non-parallel to a strap/strapping in order to deflect a pair of commercial scissor blades into an angle of incidence to the strap and the spacing between each obstacle being configured to be less than a total thickness of the scissor blades in order to jam a pair of scissors there between. Embodiments may include a dual row of semicircular millimeter obstacles (plates) having opposing concave surfaces, each endpoint of a semicircle in a first row configured to be adjacent an apex of a semicircle of a second row, each endpoint spaced apart from a surface of another obstacle plate by a thickness of a single blade of a pair of common commercial scissor blades. The protective garment also comprises a plurality of cut obstacle elements disposed on the strapping, each cut obstacle element disposed adjacent a pair of plate endpoints and a convex side of the plate pair. The protective garment further comprises a waist strap, a crotch strap and a strap for each thigh disposed at an outer respective edge of the garment, each strap comprising a non-elastic material, the dual row semicircular plate strapping and the cut obstacle elements permanently disposed there around configured to deflect a pair of scissor blades at the strap into a double obstacle cutting position.

The disclosed garment comprises a flexible and elastic ergonomic material suitable for everyday wear. The garment comprises a cut impedance strapping comprising a plurality of substantially thin and curved steel cut-resistant plates coated with plastic and/or reinforced plastic elements, spaced apart in a scissors cut obstacle deflecting pattern, the spacing configured to be up to 2.0 millimeters. The garment may also comprise a cut impedance strapping comprising a plurality of substantially flat cut-resistant millimeter plates spaced apart in a scissors cut deflecting pattern, the spacing configured to be less than a total thickness of two scissor blades. The disclosed garment additionally comprises a waist strap, a crotch strap and a strap for each thigh, each strap comprising the strapping permanently attached to an undergarment and an outer respective edge of the undergarment. This creates a fortified scissors blade obstacle deflecting skeleton frame of the undergarment. Also, each strap may be configured to have an adjustable girth via a lock. An elastic sub-portion connects an end of each strap to another portion of the strap. The elastic sub-portion is overarched by a non-elastic strapping portion which renders the entire strap non-elastic when joined into a loop via the lock.

The disclosed cut impedance strapping may comprise a plurality of millimeter cut-resistant metallic and composite strings configured in a to dimensional wave resembling the dual row of semicircular millimeter steel plates having opposing concave surfaces above, the spacing between waves configured to be less than a total thickness of two scissor blades in an ergonomic and cut deflecting pattern as disclosed herein. The strapping comprising the wave string may also be disposed as a ribbing on the undergarment support and on the undergarment itself and thereby substantially delay or impeded undesirable undressing.

Other aspects and advantages of embodiments of the disclosure will become apparent from the following detailed description, taken in conjunction with the accompanying drawings, illustrated by way of example of the principles of the disclosure.

Throughout the description, similar and same reference numbers may be used to identify similar and same elements depicted in multiple embodiments. Although specific embodiments of the invention have been described and to illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the claims.

The term 'obstacle' as used throughout the present disclosure refers to a spreading pattern of steel elements covered or coated with plastic (or reinforced plastic) and with plastic or reinforced plastic and/or steel elements/plates to prevent a straight cut and to inhibit a shearing by scissors. The term 'deflecting' as used throughout the present disclosure refers to sliding or a slipping aside or a turning/twisting of a pair of scissor blades from a straight course at an angle of incidence orthogonal to a garment strap comprising steel elements covered or coated with the plastic or reinforced plastic and/or reinforced plastic elements. The term 'jamming' refers to an obstacle lodging between the blades of a pair of scissors and impeding or preventing movement of the blades. The term 'angle of incidence' as used throughout is a measure of deviation from a 'straight on' approach of a pair of scissors to cutting a garment border, strap and/or strapping. Therefore, an angle of incidence with respect to a pair of scissor blades includes acute approach angles to the garment and obstacles attached or embedded therein/thereon due to the shearing action of the blades in a plane substantially orthogonal to the garment. That is, an acute angle of incidence of each blade with respect to a complementary surface of the garment in a shearing action may also tend to push the obstacles away from the scissors and thereby further impeded and deter an assault on the garment wearer. The terms 'garment' and 'undergarment' refer to any article of clothing worn against the body such as underwear and any article of clothing worn over clothing on the body such as outerwear including shorts, sports tights, etc including an item comprising only the waist strap, both thigh straps and a crotch strap as described herein. The term 'chamfered' refers to a beveled edge connecting two surfaces at right angles, typically at 45 degrees. The term 'beveled' used throughout the present disclosure refers to a reduction of an otherwise edge of an obstacle to a sloping and/or curved surface. The term 'torsional' may refer to the twisting of a body by two equal and opposite torques coming from the blades of a pair of shears or a pair of scissors.

Additionally, the term 'spacing thickness' refers to steel elements covered or coated with plastic or reinforced plastic and/or plastic/reinforced plastic elements and/or steel elements spaced apart in a scissors-cut obstacle deflecting pattern as disclosed herein, the spacing configured to be up to 2.0 millimeters vertically (between plates) and up to 1.5 millimeters vertically (between rows) or in any other applicable space. A pattern using reinforced plastic may include smaller and more crowded pieces/elements while steel guard plates may be spaced as aforementioned. The term 'steel elements or steel plates covered or coated with plastic or reinforced plastic' refers to small thin (0.4 to 1.0 millimeter) flat or curved pieces of steel of any shape, size and design, covered or coated with various types of plastic and/or reinforced plastic during the production process using injection molds which create a strong connection of the steel elements and the fabric by allowing the plastic to penetrate and go through the strap fabric. Also, an ultrasonic soldering and/or ultrasonic welding may be used to create a strong and durable connection attaching the plastic or the reinforced plastics and the coated steel with the strap fabric. The term 'plastic elements' or 'reinforced plastic elements' refers to small thin flat or curved obstacle element pieces in various shapes and sizes made of plastic or reinforced plastic attached to the strap by injection molding and/or by ultrasonic soldering and/or ultrasonic welding. The term 'steel plates' or 'steel elements' refers to thin elements, obstacles or plates made of steel or any other cut resistant material in a semicircular shape or of any other applicable shape and design attached to the strap by a plastic coating using injection molding, or with a type of adhesive material, a stud or in any other applicable manner. The term 'crotch strap' refers to non-elastic fabric including cut resistant fabric attached to the middle section of to the elastic and ergonomic material of the garment covering part of the middle area from the waist line of the back side downwards to the crotch and up to the front waist line of the stomach side including the obstacle deflecting elements.

An embodiment depicted in the present disclosure shows a one piece crotch strap. However, the term 'crotch strap' may refer also to a kind of body covering that may be fabricated from some pieces of straps and various fabrics. The term 'waist strap' and 'thigh straps' or 'strap for each thigh' comprise mainly non-elastic fabric portions which may comprise the obstacle deflecting elements and smaller elastic sub-portions allowing adjustable girth. Another portion of non-elastic strap may also comprise the obstacle deflecting elements knitted to the undergarment inner side at the waist area and to the non-elastic portion of the first mentioned strap. The non-elastic strap portion may be located so it overarches the elastic sub-portion. The non-elastic portion may also be designed so the other side of the non-elastic portion is fixed with an adjustable lock to the other edge of the non-elastic portion of the first mentioned loop strap and therefore renders the entire strap non-elastic when joined into a loop via the lock. The terms 'straps' or 'strapping' refer to the waist strap, the crotch strap and both thigh straps, each include the scissors obstacle deflecting steel elements covered with plastic and/or reinforced plastic and/or reinforced plastic/plastic elements and/or steel plates, steel elements or string dimensional waves. The obstacle elements may be strongly connected to the strap by plastic fully or partially penetrating the strap using injection mold or ultrasonic technology, a stud or an adhesive.

An embodiment is disclosed comprising a practical garment, in particular an undergarment, which can be efficiently used as impediment against sex assault. The garment combines two features opposing in their nature. One feature may include a soft, ergonomic, flexible and elastic (at least in substantial parts) material and another feature may include strength, durability and resistant to a forcible attempt of pulling and to a scissors shearing.

Prior art may not include one or both of the aforementioned features; those which are based only on a cut resistant fabric for covering the entire structure of the undergarment, such as Kevlar, do not provide a required degree of ergonomic elasticity for comfortable and sustained wear. Also, a suitable thickness of such fabric, as required for an undergarment, does not provide to sufficient resistance to shearing in circumstances of excessive force and violence when professional grade scissors are used. Therefore, such art which includes features for delaying undressing by pulling will have very limited results as the undergarment can be removed by common scissors. Unlike prior art, the disclosure comprises mainly ergonomic-elastic fabrics while only the waist, thigh and wide crotch straps comprise mainly non elastic cut resistant fabrics (waist and thigh straps include a small part which is elastic in order to ensure that straps are properly ergonomic fitting the wearer and a short overlapping strap for eliminating the elasticity once the straps are fitted and adjusted).

Other prior art, based on metal meshes are unlikely to match the level of comfort, ergonomic fit, flexibility or level of thickness that the disclosure provides for protective, efficient and fitting daily use. Others which are based on belts (waist and vertical) made of leather or iron are not ergonomic, with excessive thickness unfitting an undergarment for daily use. Furthermore belts have a structural weakness point due to its narrow coverage of the crotch which allow undressing by pulling (shifting aside) of the vertical belt resulting in no protection.

Other possible relevant art relates to cut resistant fabrics not designed for soft and ergonomic undergarments let alone preventing scissors shearing of the same. In addition, prior art based on the fabric itself (such as Kevlar) are based on multiple layers of same pattern elements and plates to prevent punctures and knife cuts on a broad area. However, the present disclosure includes a method of obstacle protection of one or two rows and up to several rows of elements located mostly in the outer side (edge) of the undergarment straps.

Embodiments of the present disclosure include scissors shearing obstacles embedded in an ergonomic undergarment with up to 3 straps comprising spaced elements which may be varied in shape, texture, thickness and size. The obstacles may be fixed to the fabric by plastic coating and injection molding or by glue on one side or embraced onto the strap on both sides when the obstacle elements are made of steel, or reinforced plastic. Injection molding the obstacle elements directly onto or into a strap on both sides creates an optimum scissors shearing obstacle and a shearing or cutting impediment and scissors blades deflection.

The obstacle elements are concentrated only in certain areas of the undergarment on a minimum spreading area in order to provide an ergonomic undergarment which is protective from an aggressive attempt of undressing against the wearer's wish. Due to the small coverage area of the obstacle—the impediment elements on the undergarment may be varied in design to create real shearing obstacles that could not be achieved if such patterns were embedded in broader areas of the undergarments without having such undergarment becoming bulky and less ergonomic. The combined obstacle deflecting strapping of the disclosure is structured in a way that any type of undressing to enable forced intercourse requires overcoming at least one strapping impediment.

The present disclosure does not focus on creating a fabric per se which is cut-injury resistant, but provides features to prevent a considerable cut off of the undergarment via an impediment structure, incorporated particularly in the waist strap, thighs straps and crotch strap. The straps may all be interconnected in an embodiment of the disclosure for ergonomic daily use of the undergarment. Also, the disclosure includes a structural impediment or obstacle for preventing an aggressive undressing attempt by pulling the undergarment of a wearer.

The disclosed protective undergarment may be made of an elastic ergonomic material covering a wearer from his or her waist to their thighs. The garment may comprise a cut resistant (Kevlar of Dynemma) strapping with small elements made of steel, covered (coated) with reinforced plastic or plastic-like materials closely spread in a scissors shear obstacle manner. This disclosed design causes the blades to deflect, slip over the obstacle element or to cause the strap/elements to twist under the forced shearing jamming of the same between the blades. Also due to their small size and dense spreading, the obstacle elements may avoid being split or cut especially in the case of slim curved steel plates.

The protective garment may also comprise a waist strap, a wide crotch strap and a strap for each thigh disposed at an outer respective edge of the garment, each strap comprising a non-elastic but flexible cut resistant material and the obstacle rows of plastic elements and or the coated steel plates strapping permanently disposed there around configured to deflect a pair of scissor blades at the strap into a different cutting position.

Figure 1:
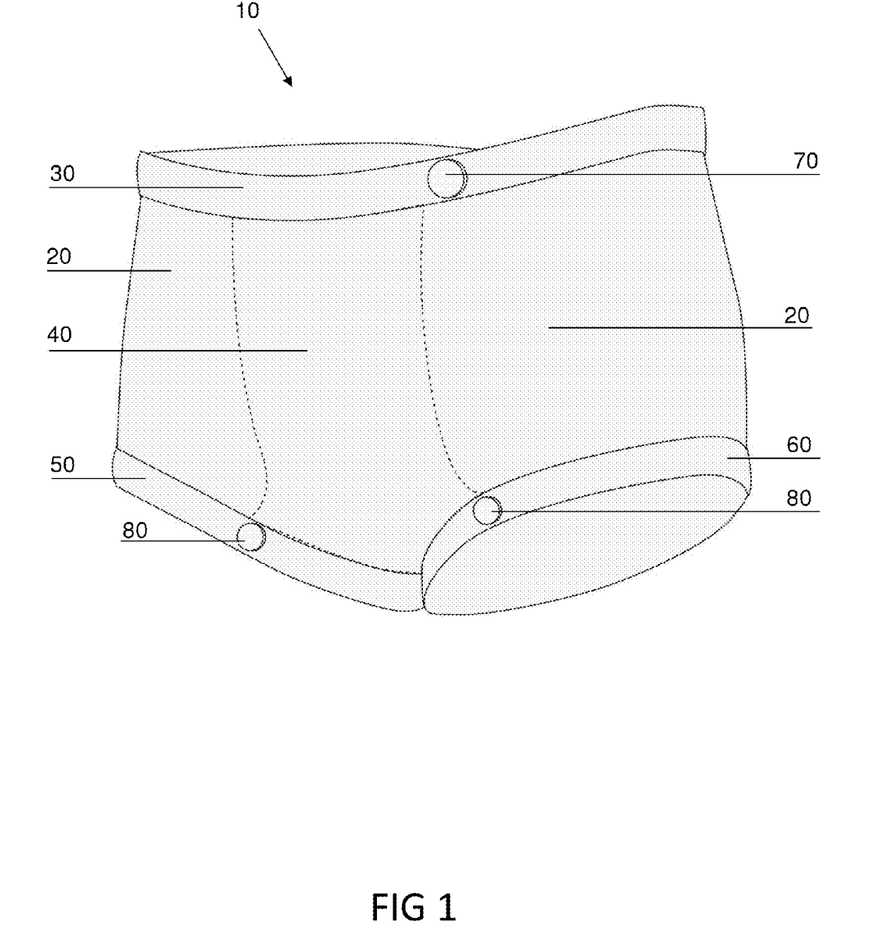
FIG. 1 is a front perspective depiction of a protective garment with scissor deflecting and jamming obstacles showing straps and strap locks in accordance with an embodiment of the present disclosure.

FIG. 1 is a front perspective depiction of a scissors deflecting protective garment showing straps and strap locks in accordance with an embodiment of the present disclosure. A protective garment 10 of elastic ergonomic material 20 covers a wearer from his or her waist to their thighs. The protective garment also comprises a waist strap 30, a crotch strap 40 (depicted in broken lines) and a strap for each thigh 50 and 60 (which are all covered with ergonomic material 20) disposed at an outer respective edge of the garment 10. The protective garment 10 further comprises a waist strap lock 70, a left thigh strap lock 80 and a right thigh strap lock (also 80). Locks and components thereof may be located within the ergonomic material which covers the waist and the thigh strap. A protective garment may also comprise underwear, shorts, tights, etc.

A lock for the waist strap may be configured to open via a two-handed and relatively gentle operation from an inner side of the strap adjacent the wearer's body. This feature may deter an attacker who is holding a weapon with one hand and therefore unable to open the lock with their other hand or help a victim to get loose of the attacker hold/grip having a better chance defending and escaping. However, a wearer of the disclosed garment may of course use both hands to open the lock and adjust the waist girth of the waist strap band/loop 30. However, a lock 80 and 90 for each thigh strap are configured to be more difficult to open and may open only with a help of a designed tool usually after underwear are safely removed. The thigh lock should not be opened for repeating use. Once the thigh loop strap is adjusted to a comfortable position and locked, the cone shape of the thigh will prevent the underwear from being lifted up to reveal intimate body area but may not prevent the underwear from being pulled down. Therefore the wearer may not take off the underwear without opening the thigh lock. In an embodiment of the disclosure, the lock 80 and 90 for each thigh strap may also open via a one-handed semi-permanent operation from an outer side of a respective strap adjacent the wearer's body. This feature allows convenient adjustment by a wearer where a two handed adjustment on a thigh strap may not be practical.

An embodiment comprises a protective undergarment support for a wearer from his or her waist to their thighs, comprising a cut impedance strapping comprising a plurality of substantially steel elements or plates covered by plastic to or by reinforced plastic or reinforced plastic/plastic elements. The elements may be cut-resistant obstacles, elements or plates spaced apart in a scissors-cut deflecting pattern as disclosed herein, the spacing configured to be less than 2 millimeters or less than a total thickness of two scissor blades. The embodiment further comprises a waist strap, a wide crotch strap and a strap for each thigh, each strap comprising the strapping permanently attached to an outer edge of the undergarment, the waist and thigh straps configured to have an adjustable girth via a lock.

Figure 2:
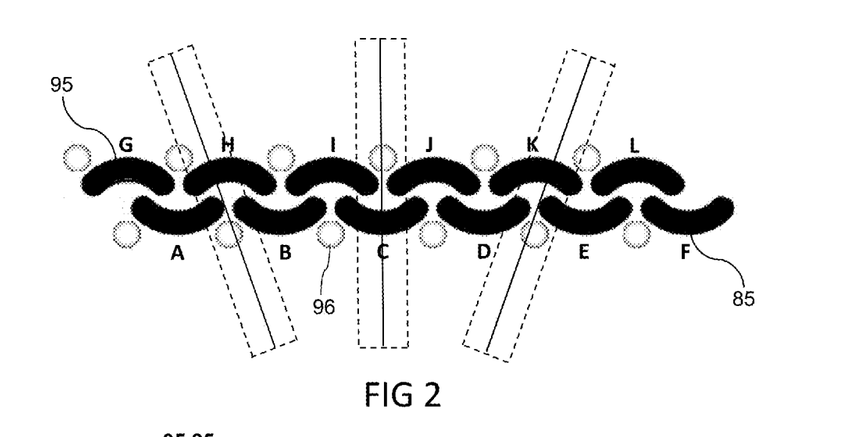
FIG. 2 is a close-up view of the scissors deflecting and jamming obstacles embedded in the strapping in accordance with an embodiment of the present disclosure.

FIG. 2 is a close-up view of the scissors deflecting obstacle strapping comprising steel elements covered with plastic embedded in the strapping in accordance with an embodiment of the present disclosure. The strapping comprises a dual row of semicircular millimeter obstacle plates having opposing respective concave surfaces 85 and 95. That is, the concave surfaces of the first row of semicircular plates A, B, C, D, E and F oppose the concave surfaces of the second row of semicircular plates G, H, I, J, K and L. In other words, the first row of semicircular plates is interleaved with the second row of semicircular plates in a pattern obstructive to a straight cut with a pair of scissors. The obstacles or deflecting elements may also be configured in rounded edge rectangle shape and even in a one row pattern where the obstacle element shape creates an obstacle for the scissors to go through. This embodiment includes reinforced plastic elements 96 in a rounded dome shape located adjacent the 2 millimeter space between the semicircular coated steel elements. The dome shaped elements may also comprise a substantially flat surface adjacent an underside of the garment. The placement of the dome shape element 96 increases the likelihood the scissors blades may deflect, slip aside or cause the elements and fabric to jam between scissors blade during the attempt of shearing the strapping. This jamming action may cause substantial delay of undesirable undressing. In alternate embodiments, semicircular obstacle plates may be configured in one of a sinusoidal shape and an elliptical shape.

In an embodiment of the present disclosure, the plastic and reinforced plastics and cover elements may be disposed on the non-elastic material and held thereon by injection molding which allows the plastic to go through the strap and finally hold it in one piece on both sides of the fabric. Each to of the obstacle elements and/or plates may also be beveled to avoid any sharp edges and adjacent plates are chamfered to also prevent any sharp edges and snagging points to the substrate material and the wearer of the protective garment. Also, each semicircular steel element may be disposed on the non-elastic material and held thereon via a stud extending through the material. Alternative methods and materials are also comprised in disposing the obstacle deflecting elements and/or plates onto the material substrate such as adhesives and molecular bonding resulting from placement of metallic and/or composite molten forms directly on the fabric material.

Each endpoint of a semicircle in a first row is configured to be adjacent an apex of a semicircle of a second row, each endpoint spaced apart from a surface of another plate by a thickness of up to 2 millimeters or up to a single blade of a pair of scissor blades. An embodiment of the disclosure includes each endpoint spaced apart from a surface of another plate or endpoint by 1 mm to 2 mm (between the plates in a row) and up to 1.5 mm between two rows plus or minus a ten percent manufacturing tolerance. This spacing corresponds to the thickness of a single blade of a pair of scissors of 1 mm plus or minus a ten percent manufacturing tolerance. Also, the semicircular elements (the steel and the plastic coating) measure a nominal 1.0 mm to 2.0 mm thick by a nominal 5 to 15 mm in length and 3 to 5 mm in width plus or minus a ten percent manufacturing tolerance. A 0.4 to 1 mm thickness and 5-13 in length and 3-4 mm in width of steel may be covered with the plastic or reinforced plastic with an average coating layer of 0.5-2 mm. In other words, an end point of each plate A and B are adjacent the apex of semicircular plate G. Specifically, the concave surface of plate A opposes the concave surfaces of plates H and G and so forth. The plastic or reinforced plastic elements which are located on top (or below) the spaced thickness between the semicircle elements, is a 4-6 mm diameter and of 1.0-1.2 height (at the apex). Each strap comprises a non-elastic material and the dual row semicircular elements strapping and dome elements permanently disposed there around configured to deflect a pair of scissor blades at the strap into a double plate cutting position as is detailed below.

The broken line rectangles in FIG. 2 represent scissor blades as seen from a top perspective. The thickness of the scissor blades are relative to the to spacing of the obstacle deflecting elements or plates. A scissor cut attempted in the middle position is unstable because each of the blades have an angle of incidence to the plates B and C. Therefore, the scissor blades may be deflected into either the left or the right stable positions (space between plates B and C or C and D respectively) where the scissor blades may have a straight approach to plates A and E respectively. However, as can be seen, the scissors at either the left or the right radial positions must cut through two plates and a plastic element rather than a single plate in the middle position. Scissors for cutting metal equipped with relatively thick blades, thicker than the space between the deflecting plates, must cut a first row of the coated steel plates before cutting the full width of the second row of coated steel plates. A scissor cut at any location other than the apex of plates A, B, C or D may be unstable because the blades will tend to slide from the respective apex of the plastic elements toward a radial position and/or a spaced position with respect to a particular plate. In other words, the scissors may be deflected into a space between plates where the scissors are forced to cut through at least 2 obstacles. Therefore, the disclosed dimensional wave strings or the semicircular coated steel plates and the dome shaped plastic elements deflect and prevent or at the very least deter a scissor cut at the strapping and stop and/or slow down an assault.

Therefore, a scissors assault on a wearer of the disclosed garment is distinguished from a knife assault. A scissor cut with two opposing blades includes acute approach angles to the borders of the garment and obstacles attached or embedded therein/thereon due to the shearing action of the blades in a plane substantially orthogonal to the garment. That is, an acute angle of incidence of each blade with respect to a complementary surface of the garment in a shearing action may also tend to push the obstacles having convex surfaces away from the scissor blades and thereby further impeded and deter an assault on the garment wearer. That is, a longitudinal component of the scissor shearing force acts on a curved or angled surface of the garment cut obstacles but cannot find a straight-on surface to take hold. The scissor blades therefore deflect from the obstacle and/or push the obstacle away from the blades. Both blades may encounter a deflecting obstacle but only one blade on one side of the garment is necessary to deflect the scissors.

Figures 3A, 3B:
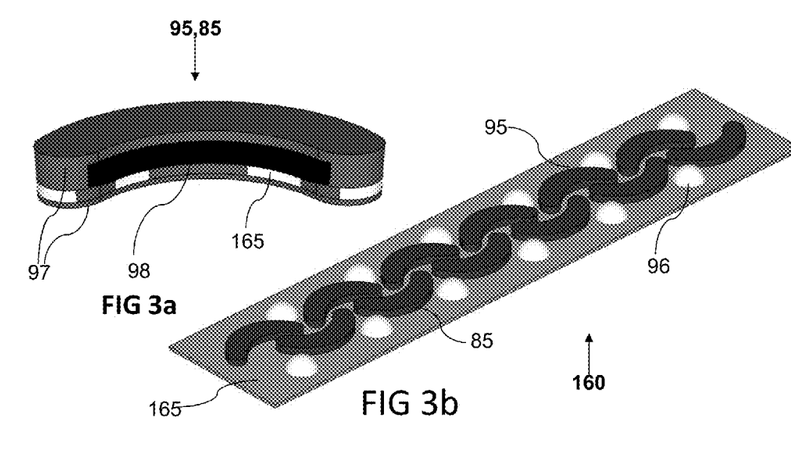
FIG. 3a is a close-up perspective view of the scissors obstacle deflecting steel element coated with plastic broken down to its components which are embedded in the strapping in accordance with an embodiment of the present disclosure.
FIG. 3b is a perspective view of the strap comprising obstacle deflecting steel elements covered with plastic or reinforced plastic and further elements made of plastic (of the coating plastic type) in accordance with an embodiment of the present disclosure.

FIG. 3a is a close-up perspective view of the scissors obstacle deflecting steel element coated with plastic broken down to its components which are embedded in the strapping in accordance with an embodiment of the present disclosure. Throughout the present depiction, similar and same reference numbers may be used to identify similar and same elements depicted in other figures of multiple embodiments. The close-up cut-away view of the scissors obstacle deflecting steel or metallic element 98 coated with plastic, shows the plastic 97 covering and penetrating through the fabric 165 (also known as strapping material) which is embedded in the strapping in accordance with an embodiment of the present disclosure.

FIG. 3b is a perspective view of the strap comprising obstacle deflecting steel elements covered with plastic or reinforced plastic and further elements made of plastic (of the coating plastic type) in accordance with an embodiment of the present disclosure. Throughout the present depiction, similar and same reference numbers may be used to identify similar and same elements depicted in other figures of multiple embodiments. The non-elastic strap 160 comprises obstacle dual row deflecting steel elements of the first row 95 and of the second row 85 covered with plastic or with reinforced plastic connected to a non-elastic fabric strap 165, and the penetration of the plastic though the strap holding of both sides; in addition, a view of the elements made of plastic (of the coating plastic type) 96.

Figure 4:
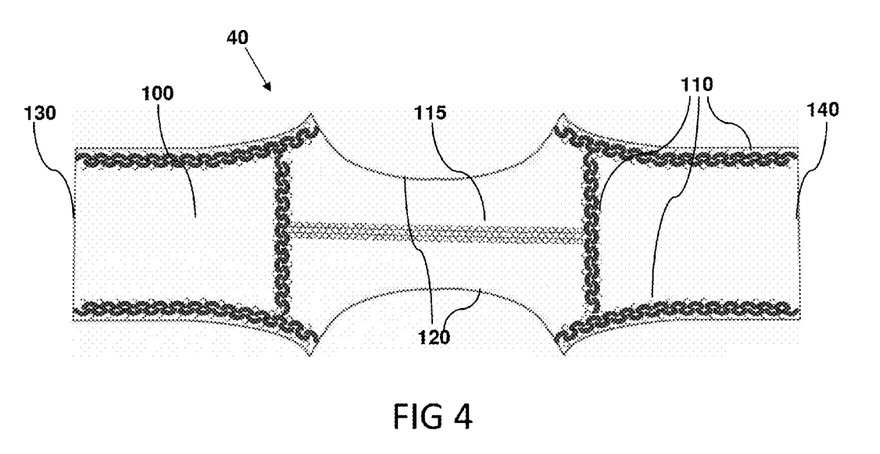
FIG. 4 is an elevational depiction of a crotch strap comprising the scissors deflecting plate strapping having steel elements covered with plastic and plastic elements in accordance with an embodiment of the present disclosure.

FIG. 4 is an elevational depiction of a crotch strap comprising the scissors deflecting plate strapping having steel elements covered with plastic thereon in accordance with an embodiment of the present disclosure. Throughout the present depiction, similar and same reference numbers may be used to identify similar and same elements depicted in other figures of multiple embodiments. The crotch strap 40 comprises a non-elastic cut resistant fabric material 100 and the protective scissors deflecting obstacle strapping elements 110 at its edges and in partial areas of the middle section which include both steel covered by plastic and only reinforced plastic obstacle deflecting pattern 115 except where it is adjacent thigh straps 50 and 60 along edges 120. The crotch strap 40 is configured to permanently attach to the undergarment from a front edge 130 and/or a front portion of the waist strap 30 and to attach to a rear portion of the waist strap 30 at to the points 140. The crotch strap 40 is configured to permanently attach at points 120 to a portion of each thigh loop or strapping 50 and 60 in a crotch area where the thigh loops are closest each other. Besides the attachment to the waist and thighs straps, the crotch strap 40 is entirely attached to inner side of the garment ergonomic fabric. The crotch strap 40 may further comprise ventilation notches and/or perforation holes for undergarment breathing. A pad (not depicted) may be configured to attach to the crotch strap in a front portion of the undergarment, the pad comprising cushioning and absorbent materials.

Figure 5:
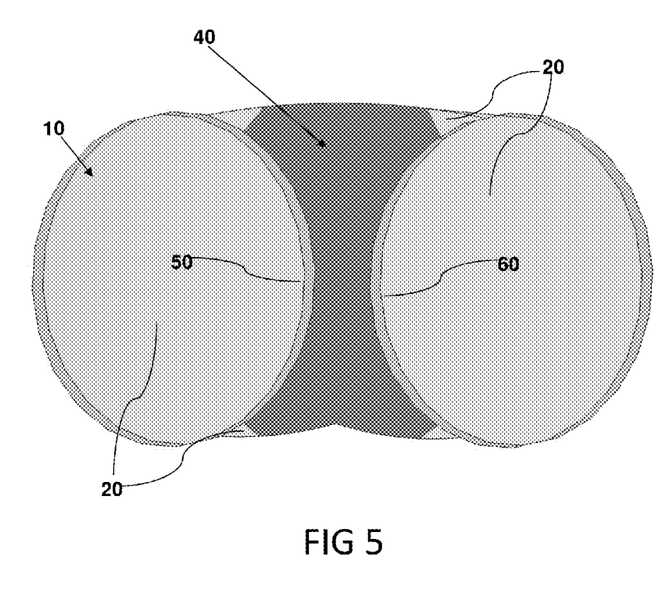
FIG. 5 is a bottom perspective depiction of a scissors obstacle deflecting protective garment showing a crotch strap and thigh straps (locks are to not shown) in accordance with an embodiment of the present disclosure.

FIG. 5 is a bottom perspective depiction of a scissors obstacle deflecting protective undergarment showing crotch strap 40 and thigh straps (locks are not shown) in accordance with an embodiment of the present disclosure. Throughout the present depiction, similar and same reference numbers may be used to identify similar and same elements depicted in other figures of multiple embodiments. The thigh straps are connecting with the thigh strapping 50 and 60, the undergarment elastic ergonomic fabric 20 (in fair gray) is viewed both in an outer side of the fabric and viewed through the thighs loops (sleeve). Thigh strapping 50,60 is viewed in medium gray (although in actual embodiment the straps might be located within sleeve of ergonomic elastic fabric); this depiction is displaying the location of the crotch strap located in the undergarment showing the strapping connection of the crotch straps with the thigh straps in accordance with an embodiment of the present disclosure.

Figure 6A:
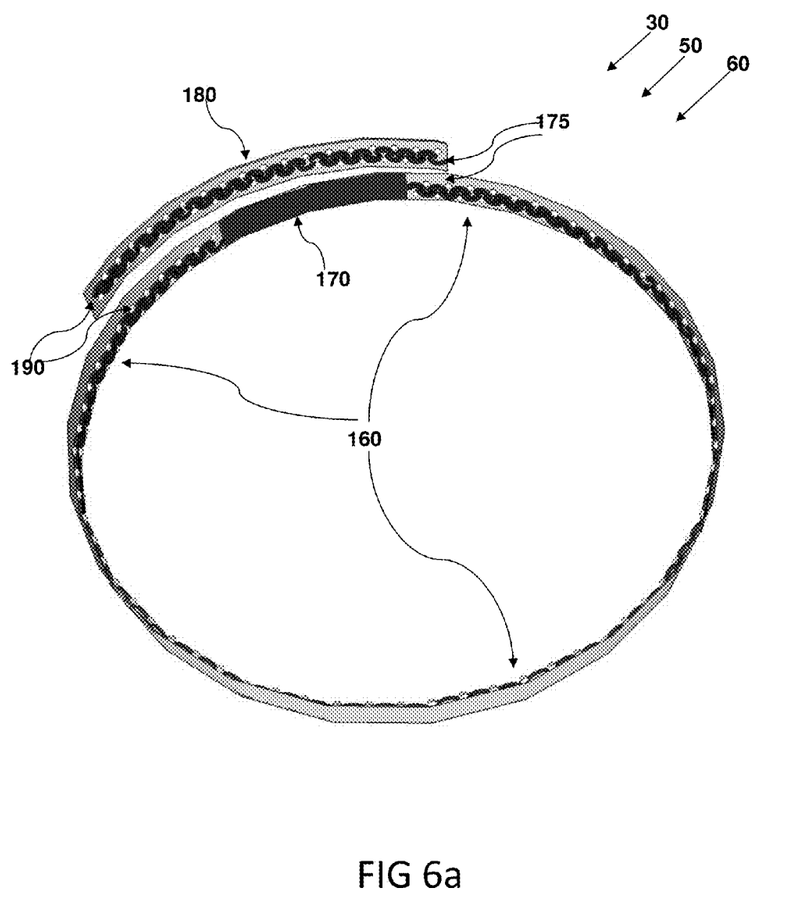
FIG. 6a is a depiction of the waist and thigh straps comprising an elastic portion with a portion overarching the elastic portion and scissors deflecting obstacle strapping having steel elements covered with plastic in accordance with an embodiment of the present disclosure.
Figure 6B:
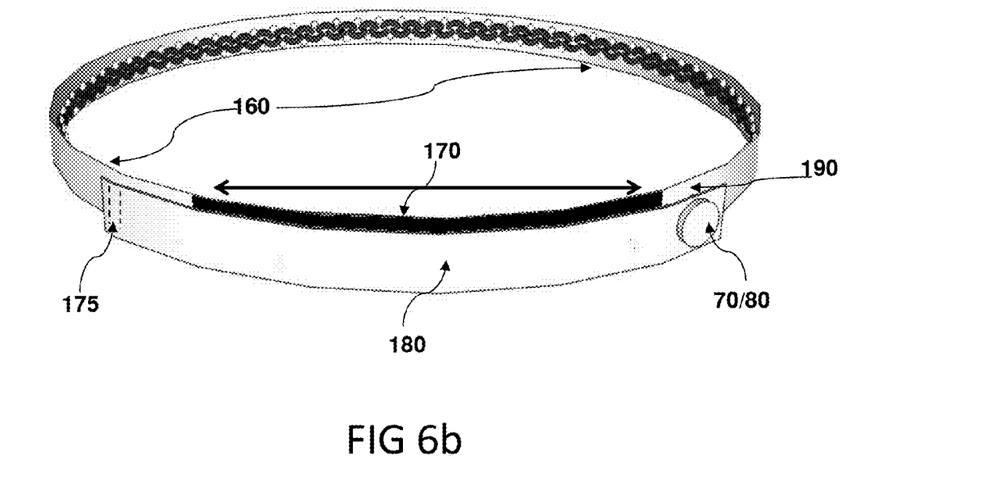
FIG. 6b is a depiction of the scissors deflecting waist strap and thigh strap with a portion overarching the elastic portion and locked into a stretched loop in accordance with an embodiment of the present disclosure.
Figure 6C:
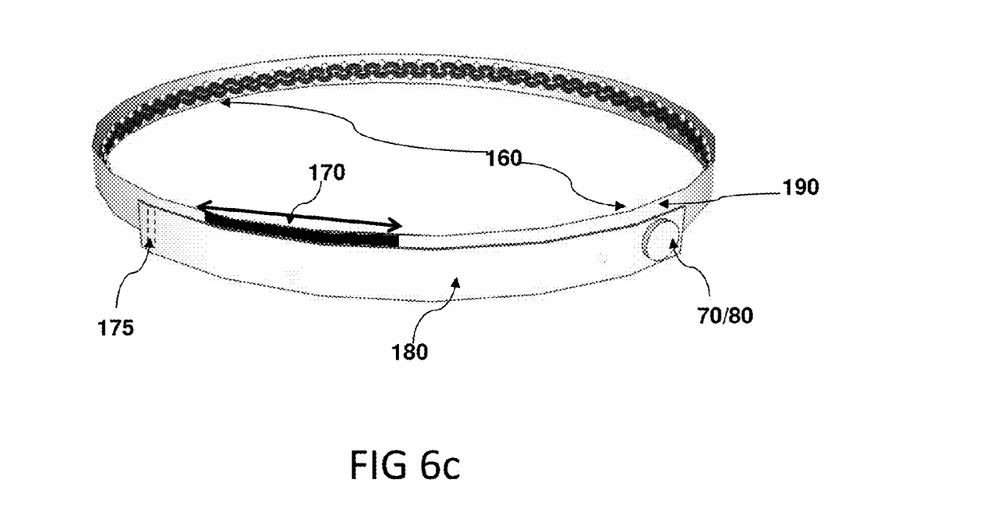
FIG. 6c is a depiction of the scissors deflecting waist and thigh strap with a portion overarching the elastic portion and locked into a tight loop in accordance with an embodiment of the present disclosure.

FIG. 6a is a depiction of a waist and thigh strap comprising mainly non-elastic position and smaller elastic portion and scissors deflecting strapping having steel elements covered in plastic and plastic elements accordance with an embodiment of the present disclosure. Throughout the present depiction, similar and same reference numbers may be used to identify similar and same elements depicted in other figures of multiple embodiments. The steel elements may optionally be comprised of any metallic element and a plastic hybrid thereof. The waist strap 30 and each thigh strap 50 and 60 have the same loop-strap structure comprising mainly non elastic portion 165 which comprises the scissors obstacle deflecting elements configured to have an adjustable girth via an elastic sub-portion and an adjustable respective lock 70 and 80 (not depicted). The girth of each strap loop 30, 50 and 60 is adjustable via an elastic sub-portion 170 connecting an end of a respective strap to another portion of the strap. The elastic sub-portion 170 is overarched by a strapping portion 180 entirely knitted to the undergarment inner side at the waist area which also comprises the obstacle deflecting elements connected to the non-elastic portion of the strap on spot 175. This renders the entire respective strap 30, 50 and 60 when joined (spot 190) into a non-elastic loop when joined into a loop via the respective lock 70 or 80. A latching portion 190 of the non-elastic waist strap latches into the lock 70 when inserted therein. Either the lock 70 placement is adjustable or the latching portion 190 is adjustable thereon in order that a wearer may adjust the girth of the waist strap loop/band for the best protective and best ergonomic fit. All strap 160 parts 30, 170 and 180 including parts of the locks are located within the waist and thighs garment lining; after fitting the right loop size to the wearer waist or thigh, the lock is inserted one part from the garment inner side and the other from the outer side of the garment through the latching portion (not depicted).

FIG. 6b is a depiction of the scissors deflecting waist and thigh strap with a portion overarching the elastic portion and locked into a stretched loop in accordance with an embodiment of the present disclosure. Throughout the present depiction, similar and same reference numbers may be used to identify similar and same elements depicted in other figures of multiple embodiments. A stretched strap loop may allow fitting to a larger waist and/or thigh and/or accommodate dressing and undressing according to a preference of a wearer of the disclosed protective garment. However, a strap loop that is too lose may allow the protective garment to be removed against the will of the wearer in compromising situations so caution should be taken to avoid overly liberal adjustments.

FIG. 6c is a depiction of the scissors deflecting waist and thigh strap with a portion overarching the elastic portion and locked into a tight loop in accordance with an embodiment of the present disclosure. Throughout the present depiction, similar and same reference numbers may be used to identify similar and same elements depicted in other figures of multiple embodiments. A tightened strap loop may allow fitting to a smaller thigh and/or accommodate dressing and undressing according to a preference of a wearer of the disclosed protective garment. However, there is no need for a strap loop that is too tight since the waist girth of most females from age of 14 is ultimately narrower than the pelvis bone to girth line and therefore designed to prevent undressing while the loop is closed via the lock and only fairly tightened to the waist line.

Figure 7:
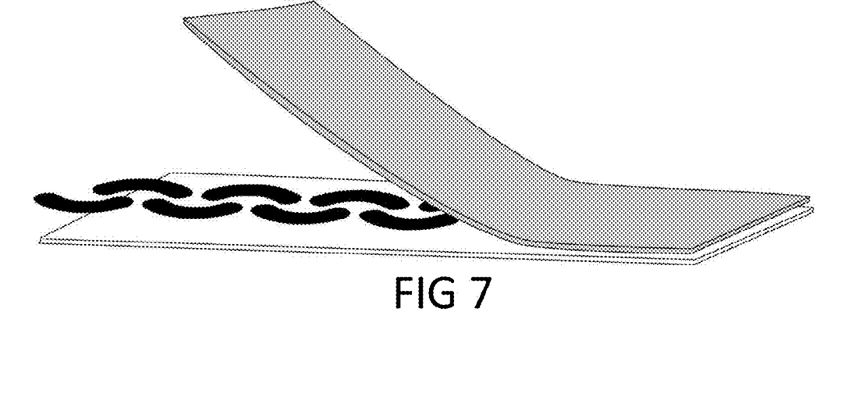
FIG. 7 is a depiction of the scissors deflecting steel obstacle element strapping between substrate and superlayers in accordance with an embodiment of the present disclosure.

FIG. 7 is a depiction of the scissors obstacle deflecting steel elements optionally covered with plastic but attached to the strap with adhesive in accordance with an embodiment of the present disclosure. The elements may be located between substrate and superlayers in accordance with an embodiment of the present disclosure. Throughout the present depiction, similar and same reference numbers may be used to identify similar and same elements depicted in other figures of multiple embodiments. Each strap may comprise the steel elements attached by adhesive and synthetic fibers embedded in a silicon substrate and a super-layer covering the strapping as a cushioning and waterproofing layer.

Figure 8:
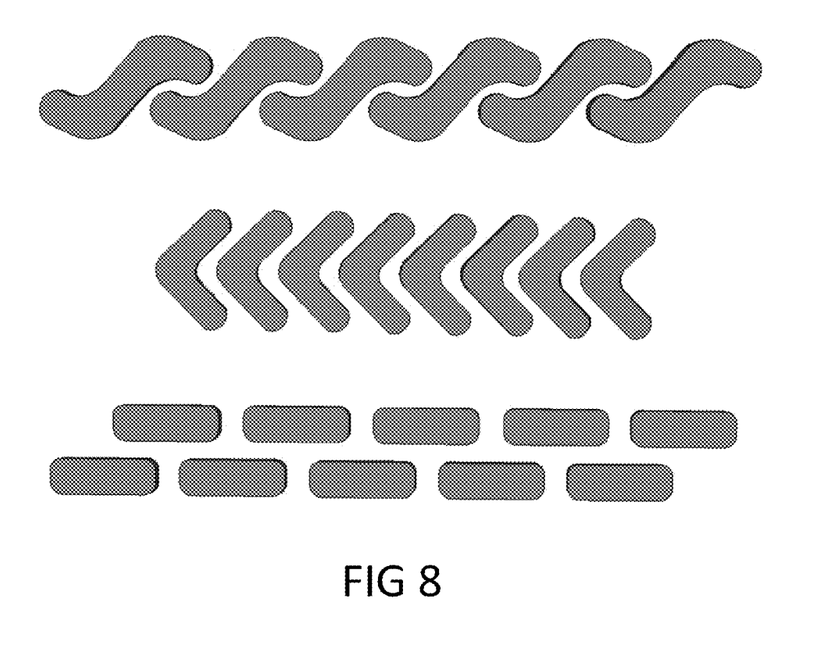
FIG. 8 is a depiction of 3 shapes and patterns of scissor deflecting obstacles which included in a strapping deflect scissors into an angle of incidence with a strap thereof and also jam the scissors in accordance with an embodiment of the present disclosure.

FIG. 8 is a depiction of 3 shapes and patterns of scissor deflecting obstacles which included in a strapping deflect scissors into an angle of incidence with a strap thereof and also jam the scissors in accordance with an embodiment of the present disclosure. Throughout the present depiction, similar and same reference numbers may be used to identify similar and same elements depicted in other figures of multiple embodiments. An imaginary line through the obstacles in series may be parallel to the strap upon which the obstacles are embedded or otherwise disposed. Therefore, the strapping may include spaced apart obstacles in series patterned to be parallel to a strap thereof. The obstacles deflect a pair of commercial scissor blades into an angle of incidence to the strap. An angle of incidence deviates from a straight on approach orthogonal to the line of depiction through the obstacles in series. Also, edges of the obstacles may be parallel and/or angular to the depiction line and parallel and/or angular to a respective strap comprising the obstacles. Therefore, the strapping has parallel obstacles patterned to have edges non-parallel to a strap thereof in order to deflect a pair of commercial scissor blades into an angle of incidence to the strap which may deviate from a straight on approach of the scissors orthogonal to the obstacles in series. A spacing between each obstacle is also configured to be less than a total thickness of the scissor blades in order to jam a pair of scissors there between and thereby impede or deter an elicit undressing thereof.

Figure 9:
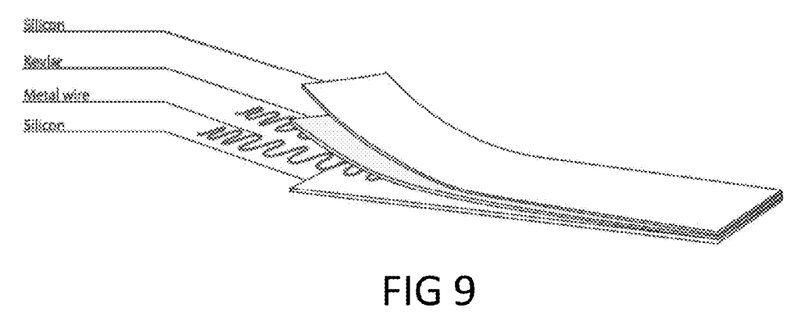
FIG. 9 is a depiction of a string dimensional wave strapping between substrate and superlayers in accordance with an embodiment of the present disclosure.
Figure 10:
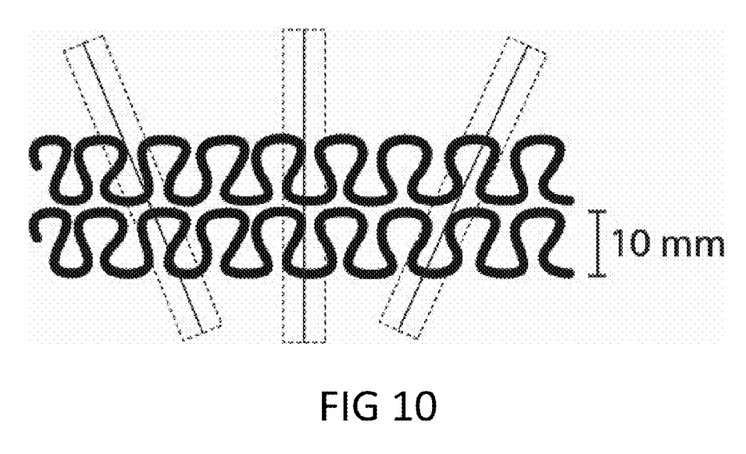
FIG. 10 is a close-up view of the scissors deflecting string dimensional wave strapping in accordance with an embodiment of the present disclosure.

FIG. 9 is a depiction of a string dimensional sinusoidal wave strapping between substrate and superlayers in accordance with an embodiment of to the present disclosure. The string dimensional wave strapping may be configured in one of a sinusoidal shape and an elliptical shape. Each strap may comprise metallic and synthetic fibers embedded in a silicon substrate and a super-layer covering the strapping as a cushioning and waterproofing layer. A plurality of millimeter cut-resistant strings may be configured in a dimensional wave spaced apart "d" in a cut deflecting pattern, the spacing "d" between waves configured to be less than a total thickness of two scissor blades. A waist strap, a crotch strap and a strap for each thigh comprise the strapping permanently attached to an outer edge of the undergarment, the waist and thigh straps configured to have an adjustable girth via a lock. The millimeter cut-resistant strings may also be configured in a dimensional wave to comprise at least one of a twisted and a spiral configuration and any other similar configuration providing a straight cut obstacle pattern to a pair of scissors within a centimeter area of the undergarment. The millimeter strings are nominally 0.4 to 1.0 millimeter in diameter and comprise metallic and synthetic materials. The strapping comprising the wave string is disposed as a ribbing on the support undergarment support and on the undergarment FIG. 10 is a close-up view of the scissors deflecting string dimensional wave strapping in accordance with an embodiment of the present disclosure. The disclosed cut impedance strapping may comprise a plurality of millimeter cut-resistant metallic and composite strings configured in a dimensional wave measuring a 10 mm wave height and resembling the dual row of semicircular millimeter steel plates having opposing concave surfaces above, the wave spacing configured to be less than a total thickness of two scissor blades in an ergonomic and cut deflecting pattern as disclosed herein. The strapping comprising the wave string may also be disposed as a ribbing on the undergarment support and on the undergarment itself.

The broken line rectangles in FIG. 10 represent scissor blades as seen from a top perspective. The thickness of the scissor blades are relative to the spacing of the millimeter wave strings. A scissor cut attempted in the middle position is unstable because the blades are non-radial to string waves B and C. Therefore, the scissor blades may be deflected into either the left or the right stable positions where the scissor blades are radial to string waves A and D respectively. However, as can be seen, the scissors at either the left or the right radial positions must cut through two string waves rather than a single string wave in the middle position. A scissor cut at any location other than the apex of string waves A, B, C or D is likewise unstable because the blades will tend to slide from the respective apex toward a radial position with respect to a particular string wave. Therefore, the disclosed millimeter dimensional wave strings deflect and prevent or at the very least deter a scissor cut at the strapping and stop and/or slow down an assault.

Therefore, a scissors assault on a wearer of the disclosed garment is distinguished from a knife assault. A scissor cut with two opposing blades includes acute approach angles to the borders of the garment and wave strings attached or embedded therein/thereon due to the shearing action of the blades in a plane substantially orthogonal to the garment. That is, an acute angle of incidence of each blade with respect to a complementary surface of the garment in a shearing action may also tend to push the cylindrical wave strings away from the scissor blades and thereby further impeded and deter an assault on the garment wearer. That is, a longitudinal component of the scissor shearing force acts on a curved or angled surface of the garment wave strings but cannot find a straight-on surface to take hold. The scissor blades therefore deflect from the wave strings and/or push the wave strings away from the blades. Both blades may encounter deflecting strings but only one blade on one side of the garment may be enough to deflect the scissors from the obstacle.

Figure 11:
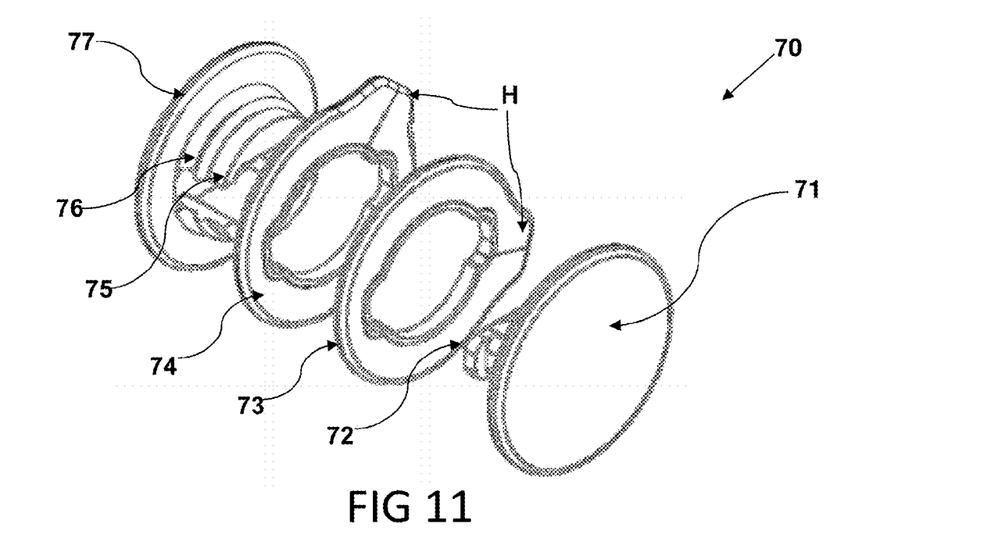
FIG. 11 is an exploded perspective depiction of a waist strapping lock showing component parts in accordance with an embodiment of the present disclosure.

FIG. 11 is an exploded perspective depiction of the waist strapping lock 70 showing component parts in accordance with an embodiment of the present disclosure. Throughout the present depiction, similar and same reference numbers may be used to identify similar and same elements depicted in other figures of multiple embodiments. The front part 71 is designed to be either located in the undergarment lining or in the outer side, and can be permanently fixed to the non-elastic strapping portion 180 which is connected to the undergarment lining from the inner side. For esthetic reasons it could be placed outside the undergarment lining, holding both the undergarment waist lining and strapping 180 or also as a detached component that will inserted by the wearer. The lock has a rectangular prominent tooth 72 which is designed to fit at a certain angle to the opening of parts 73, 74 and 77. Parts 73 and 74 are braced to part 77 and are able to rotate (clock wise) on niches 75 and 76 respectively, and are designed (parts 73 and 74) to rotation via the cams or small handles H will be at a different and offset "clock wise" point when openings of parts 73 and 74 are matching to part 72. Rear part 77 holds undergarment strapping lining within close to the wearer body holding both the undergarment lining at the waist line and strapping 160 as depicted in FIGS. 6a, 6b and 6c. The locking mechanism works by adjusting the parts so the opening of 73 and 74 are matching part 72 which is passing through all strapping (not depicted) and parts 73 and 74 and finally through the rear part 71. In this position, the undergarment wearer rotates parts 73 and or 74 and now opening niche in part 73 and or 74 will no longer be in line or offset with respect to the rectangular prominent tooth 72. Therefore it is hooked in part 77 for which it held by 73 and 74. Since there are two rotating discs (73, 74) each is planned for (at least) 12 stops as similar to clock pointers (hours and minutes), the random rotation of the two discs allows 144 combinations to open the lock. The lock components may be made of steel and resist also a very strong pulling by an attacker. Multiple amount of locks may be produced for each of the 144 combination and may be randomly assembled to the undergarment. The wearer should remember the combination of parts 73 and 74 specific rotation for adjusting the lock for opening, in a simple fashion of remembering the "hour and minute".

In an embodiment of the disclosure, the waist strap lock comprises two rotatable disks (73 and 74) and a central hub (71) configured to pass through all strapping and the disks (73 and 74) and the straps and lock everything together. The hub comprises at least one tooth and each disk comprises a complementary notch therein configured to allow the at least one tooth to pass there through and lock when the disks are offset rotated in relation thereof.

Figure 12:
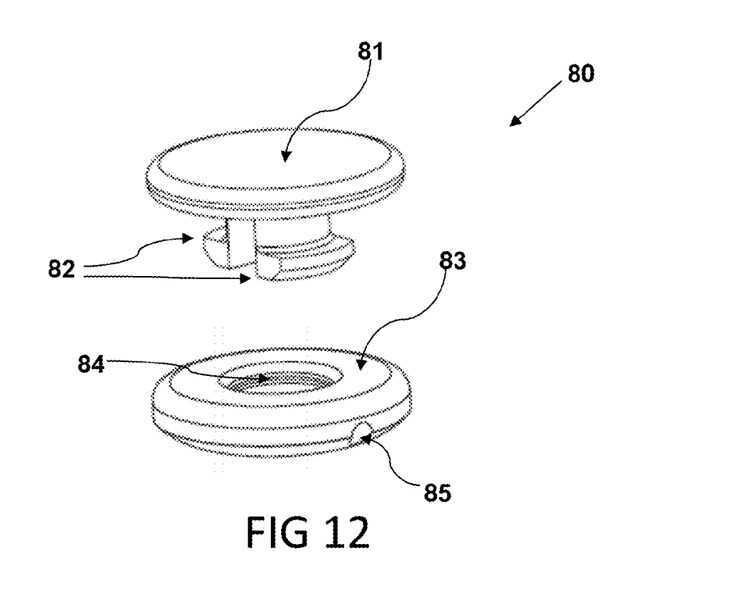
FIG. 12 is a partially assembled perspective depiction of a thigh strapping lock showing component parts in accordance with an embodiment of the present disclosure.

FIG. 12 is a partially assembled perspective depiction of a thigh strapping lock showing component parts in accordance with an embodiment of the present disclosure. Throughout the present depiction, similar and same reference numbers may be used to identify similar and same elements depicted in other figures of multiple embodiments. The waist lock 70 is designed for repeating opening, since the girth of the waist must be adjusted for each dressing and undressing. However, a lock 80 for each thigh strap is not configured for repeated use. Once the thigh loop strap is adjusted to a comfortable position and locked, the cone shape of the thigh will prevent from the underwear to be lifted up and reveal intimate body areas but will not prevent pulling down and therefore the wearer could take off the underwear without opening the thigh lock. The front part 81 is designed to be either located in the undergarment lining or in the outer side, and can be permanently fixed to the non-elastic strapping portion 180 which is connected to the undergarment lining from the inner side. But for esthetic reasons it could be placed outside the undergarment lining, holding both the undergarment waist lining and strapping 180 or can be also not connected permanently to the undergarment and inserted by the wearer when using. The mechanism of lock 80 rounded head 81 is big enough not to slip off in case of pulling. The bottom side comprises two teeth 82 that are designed to slightly approach each other while they are pushed into the opening 84 of lock 80 rear part 83 and when pushed and inserted to rear part 83, at its middle there are niche which teeth 82 are released from the squeeze and placed in that niche. Since the teeth 82 are released in the middle part of 83 there is no direct hold of 82 for squeezing by hand. The opening 84 is narrower than the girth of teeth like parts 82 lower end, therefore part 81 could not be reopened unless both teeth 82 are squeezed and pulled out. Since it is anticipated that reopening of lock 81 might be needed for various reasons, lock include tiny hole 85 of both sides of part 83 (only one side is depicted) which allow pushing each of teeth 82 using a hard wire tool with both hands at the same time. This mechanism ensures that opening will be done only under certain condition more likely under the wearer cooperation.

Embodiments of the present disclosure may further comprise a trigger wire disposed in the straps, the trigger wire configured to trigger an alarm circuit in the event an open circuit occurs anywhere in the wire. Embodiments may further comprise an ampoule disposed adjacent a front of the undergarment, the ampoule configured to broadly and forcefully disperse a bright stain and/or a bright paint and/or a deterring smell onto the undergarment and onto an attacker who cuts a trigger wire or destroys a strap lock.

Therefore, the disclosed semicircular obstacle plates, plastic elements and dimensional wave string strappings deflect and prevent or at the very least to deter a scissor cut at the strapping and stop and/or slow down an assault. The disclosed strappings prevent cutting the protective garment at the waist strap, the thigh straps and the crotch straps and yet allow an ergonomic and versatile underwear and outerwear garment for a wearer. Underpants, underwear, shorts, shirts and tights with respective arm straps and waist straps may be similarly configured per the ideas and designs of the present disclosure.

An embodiment of the disclosure comprises a strap of the disclosed strapping semicircular plates and/or the millimeter wave strings or wires which may be applied to a wearer's waist and either thigh or to an arm or neck opening of a garment independent of the respective garment. The adjustable lock therefore allows a loosening and tightening in order to accommodate the respective garment opening and provide protection against unwanted access to the wearer's body.

An embodiment of the present disclosure may also include coated steel and/or non-coated steel and/or plastic elements configured to twist in response to the torsional force of a pair of scissor blades and become lodged or jammed in between the blades or slip aside due to the small size and shape of the plates and therefore deflect a cut of the protective garment. The twisting millimeter plates are loosely configured to the garment at either end of a plate and therefore are free to twist and be torqued parallel to the scissor blades. Because of the tensile strength of the steel material comprising the millimeter plates, a plate may be forced into a parallel position with the scissor blades before it is cut. Also, due to its millimeter thickness, the obstacle elements or in some cases, plates, may therefore become lodged or jammed between the scissor blades and prevent the blades sliding adjacent each other and therefore prevent a cut of the protective garment material.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Notwithstanding specific embodiments of the invention have been to described and illustrated, the invention is not to be limited to the specific forms or arrangements of parts so described and illustrated. The scope of the invention is to be defined by the claims and their equivalents to be included by reference in a non-provisional utility application.

What is claimed is:

1. A protective garment of elastic ergonomic material covering a wearer from his or her waist to their thighs, comprising:
    a cut impedance strapping comprising a plurality of cut-resistant obstacles shaped in a scissors deflecting pattern and spaced apart in a scissors jamming pattern; and
    a waist strap, a crotch strap and a strap for each thigh, each strap comprising the strapping permanently attached to the undergarment, the waist and thigh straps configured to have an adjustable girth via a lock.

2. The protective garment of claim 1, wherein the obstacles are patterned in series parallel to a strap and comprise surfaces parallel and angular thereto to deflect a pair of commercial scissor blades into an angle of incidence to the strapping and the spacing between each obstacle is configured to be less than a total thickness of the scissor blades to jam a pair of scissors there between and thereby impede or deter an elicit undressing of the protective garment.

3. The protective garment of claim 1, wherein the obstacles comprise one of convex and beveled surfaces configured to deflect a pair of scissor blades at an angle of incidence to the garment material and at an acute angle with respect to each other.

4. The protective garment of claim 1, wherein the obstacles comprise a plastic element, a steel element and a steel element covered by one of plastic and reinforced plastic.

5. The protective garment of claim 1, wherein at least one obstacle comprises a cut resistant material formed into a dome-like structure on one side and a substantially flat surface adjacent an underside of the garment.

6. The protective garment of claim 1, wherein the waist strap and each thigh strap are configured to have an adjustable girth via an adjustable lock and the waist and each thigh strap comprise mainly a non-elastic portion including the cut obstacle elements permanently disposed thereon and a smaller elastic portion connecting an end of each portion of the strap to another non-elastic portion of the strap, the elastic portion overarched by a non-elastic strapping portion including the cut obstacle elements which renders the entire strap non-elastic when joined into a loop via the lock.

7. The protective garment of claim 1, wherein the crotch strap comprises a non-elastic and cut resistant material and the cut obstacle elements permanently disposed thereon configured to permanently attach to a front portion of the waist to strap and to attach to a rear portion of the waist strap and to both thigh straps along an inner side of the garment where the thigh loops are closest each other.

8. The protective undergarment of claim 1, wherein the crotch strap further comprises ventilation notches and/or perforation holes for undergarment breathing and a pad configured to attach to the crotch strap in a front portion of the undergarment, the pad comprising cushioning materials.

9. The protective undergarment of claim 1, wherein each strap comprises cut resistant synthetic fibers embedded in a silicon substrate and/or a water resistant material and a super-layer covering the strapping as a cushioning and waterproofing layer.

10. The protective undergarment of claim 1, further comprising a trigger wire disposed in the straps, the trigger wire configured to trigger an alarm circuit in the event an open circuit occurs anywhere in the wire.

11. The protective undergarment of claim 1, further comprising an ampoule disposed adjacent a front of the undergarment, the ampoule configured to broadly and forcefully disperse a bright colorant and/or a deterring smell onto an attacker who cuts a trigger wire or destroys a strap lock.

12. The protective undergarment support of claim 1, wherein a lock for the waist strap opens via a two-handed operation from an inner side of the strap adjacent the wearer's body.

13. The protective undergarment support of claim 1, wherein the waist strap lock comprises two rotatable disks and a central hub configured to pass through all strapping and the disks and lock the straps together, the hub comprising at least one tooth and each disk comprising a complementary notch therein configured to allow the at least one tooth to pass there through and lock when the disks are offset rotated in relation thereof.

14. The protective undergarment support of claim 1, wherein a lock for each thigh strap opens via a designed tool after the undergarment is removed from the wearer.

15. A protective undergarment support for a wearer from his or her waist to their thighs, comprising:
    a cut impedance strapping comprising a plurality of millimeter cut-resistant strings configured in a dimensional wave spaced apart in a cut deflecting pattern, the spacing configured to be less than a total thickness of two scissor blades; and
    a waist strap, a crotch strap and a strap for each thigh, each strap comprising the strapping permanently attached to an outer edge of the undergarment, the waist and thigh straps configured to have an adjustable girth via a lock.

16. The protective undergarment support of claim 15, wherein the millimeter cut-resistant strings configured in a dimensional wave comprise at least one of a twisted and a spiral configuration and any other similar configuration providing a straight cut obstacle pattern to a pair of scissors within a centimeter area of the undergarment.

17. The protective undergarment support of claim 15, wherein the millimeter strings are nominally 0.4 to 1.0 millimeter in diameter and comprise metallic and synthetic materials.

* * * * *